United States Patent [19]

Marlett

[11] 4,455,433

[45] Jun. 19, 1984

[54] PROCESS FOR PRODUCING SUBSTITUTED PYRROLES

[75] Inventor: Everett M. Marlett, Baton Rouge, La.

[73] Assignee: Ethyl Corporation, Richmond, Va.

[21] Appl. No.: 447,955

[22] Filed: Dec. 8, 1982

Related U.S. Application Data

[63] Continuation-in-part of Ser. No. 317,543, Nov. 2, 1981, abandoned.

[51] Int. Cl.³ .......................................... C07D 207/16
[52] U.S. Cl. ................................................. 548/531
[58] Field of Search ....................................... 548/531

[56] References Cited

U.S. PATENT DOCUMENTS

| | | |
|---|---|---|
| 3,752,826 | 8/1973 | Carson . |
| 3,865,840 | 2/1975 | Carson .................. 548/531 |
| 3,952,012 | 4/1976 | Carson .................. 548/539 X |
| 4,383,117 | 5/1983 | Kao et al. ............. 548/531 |
| 4,388,468 | 6/1983 | Dagani ................. 548/531 |

FOREIGN PATENT DOCUMENTS 2034304  6/1980  United Kingdom .

OTHER PUBLICATIONS

Fischer et al., Die Chemie des Pyrroles, Edward Brothers, Inc., Ann. Arbor, Michigan (1943), pp. 5, 6, 233 & 234.
Gowan et al., Name Index of Organic Reactions, Longmans, Green and Co., Ltd., New York (1960), p. 116.
Jones et al., The Chemistry of Pyrroles, Academic Press, Inc., New York (1977), pp. 59 & 104.
Krauch et al., Organic Name Reactions, John Wiley and Sons, Inc., New York (1964), p. 211.

Primary Examiner—Richard Raymond
Attorney, Agent, or Firm—Donald L. Johnson; John F. Sieberth; Patricia J. Hogan

[57] ABSTRACT

An acid having a dissociation constant of at least $1.3 \times 10^{-5}$ at 25° C. is used to enhance the yield of alkyl, 1,4-dialkyl-3-alkoxycarbonylpyrrole-2-acetate in the reaction of a chloromethyl alkyl ketone with a dialkyl acetone dicarboxylate and an alkylamine in a reaction medium comprising an organic solvent. The preferred acid is formic acid.

16 Claims, No Drawings

PROCESS FOR PRODUCING SUBSTITUTED PYRROLES

CROSS-REFERENCE

This application is a continuation-in-part of copending application Ser. No. 317,543, filed Nov. 2, 1981, now abandoned.

TECHNICAL FIELD

This invention relates to substituted pyrroles and more particularly relates to processes for preparing alkyl 1,4-dialkyl-3-alkoxycarbonylpyrrole-2-acetates.

BACKGROUND

It is known that alkyl 1,4-dialkyl-3-alkoxycarbonylpyrrole-2-acetates, sometimes simply designated as pyrrole diesters, are useful as intermediates in the preparation of 5-aroylpyrrole-2-acetic acids and derivatives having analgesic and anti-inflammatory properties. It is also known that such compounds, although difficult to prepare because of the effect of other substituents in hindering substitution at the 4-position, can be synthesized, e.g., by condensing a chloromethyl alkyl ketone with a dialkyl acetone dicarboxylate and an alkylamine.

Carson's U.S. Pat. No. 3,752,826 and its divisions, U.S. Pat. Nos. 3,865,840 and 3,952,012, show that this condensation can be accomplished in an aqueous medium, although experience has revealed that the aqueous reaction leads to the formation of solid intermediates which are difficult to agitate and present problems in controlling the exothermic reaction that occurs when the intermediates are converted to the desired product.

Copending applications Ser. Nos. 137,231 and 137,250, filed Apr. 4, 1980, in the names of Michael J. Dagani and James T. F. Kao, respectively, show that the disadvantages of Carson's process can be overcome by the use of a halogenated hydrocarbon or an aromatic hydrocarbon as a co-solvent; and Mallinckrodt's UK Patent Application GB No. 2 034 304 A also teaches advantages of using an aqueous/organic medium for the reaction.

Further improvements in alkyl 1,4-dialkyl-3-alkoxycarbonylpyrrole-2-acetate syntheses are taught in copending applications Ser. No. 293,853, filed Aug. 18, 1981, in the name of Michael J. Dagani, and Ser. No. 317,156, filed Nov. 2, 1981, in the names of James T. F. Kao and Everett M. Marlett now U.S. Pat. Nos. 4,388,568 and 4,383,117, respectively. The former application discloses that the use of elevated temperatures to dehydrate the dihydroxypyrrolidine intermediate can obviate the need for the intermediate isolation and acidification steps that had previously been used in these syntheses. The latter application teaches that problems associated with the use of the reaction media formerly employed—specifically, the solids formation problem associated with the use of an aqueous medium and the feed control problems associated with the use of a two-phase aqueous/organic medium—can be avoided by contacting the reactants in a non-aqueous organic solvent and conducting the reaction in the absence of any added water.

Both the use of an aqueous/organic reaction medium and the use of an organic solvent are commercially-attractive means of preparing the pyrrole diesters. However, with the utilization of known techniques, reactions conducted in these media lead to yields no higher than about 72%, with somewhat lower yields being more typical. It would obviously be desirable to provide a means of increasing those yields.

SUMMARY OF THE INVENTION

An object of this invention is to provide novel processes for preparing alkyl 1,4-dialkyl-3-alkoxycarbonylpyrrole-2-acetates.

Another object is to provide such processes wherein the pyrrole diesters are synthesized from a chloromethyl alkyl ketone, a dialkyl acetone dicarboxylate, and an alkylamine in a reaction medium comprising an organic solvent.

A further object is to provide a means of improving yields in such processes.

These and other objects are attained by conducting the reaction of a chloromethyl akyl ketone with a dialkyl acetone dicarboxylate and an alkylamine to form an alkyl 1,4-dialkyl-3-alkoxycarbonylpyrrole-2-acetate in a reaction medium comprising an organic solvent and in the presence of a yield-enhancing amount of an acid having a dissociation constant of at least $1.3 \times 10^{-5}$ at 25° C.

DETAILED DESCRIPTION

The chloromethyl alkyl ketone that is used in the practice of the invention may be any compound corresponding to the formula $ClCH_2COR$, wherein R is a lower alkyl group, i.e., an alkyl group containing 1-6 carbons. It is generally preferred that it be chloroacetone.

The dialkyl acetone dicarboxylate of the reaction mixture is generally dimethyl or diethyl acetone dicarboxylate, but it can be any compound corresponding to the formula:

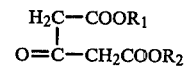

wherein $R_1$ and $R_2$ are independently selected from lower alkyl groups and are preferably the same.

The alkylamine used in the practice of the invention is a compound of the formula $R'NH_2$, wherein $R'$ is a lower alkyl group. Preferably the alkylamine is methylamine.

As indicated above, the process of the invention is conducted in a reaction medium comprising an organic solvent. Since, as is already known, the aforementioned compounds react with one another to form an alkyl 1,4-dialkyl-3-alkoxycarbonylpyrrole-2-acetate corresponding to the formula:

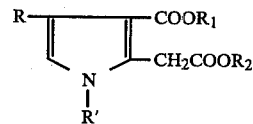

and this reaction inherently produces water as well as the pyrrole diester, the reaction medium will also comprise at least a small amount of water by the end of the reaction. Moreover, the reaction medium may comprise additional water when it is desired to provide an aqueous/organic reaction medium, such as the medium of the aforementioned Dagani (Ser. No. 137,231), Kao (Ser. No. 137,250), and Mallinckrodt references. However, it is generally preferred to employ an organic solvent as the sole ingredient of the initial reaction medium and to add no water during the reaction so as to benefit from the advantages of employing an organic solvent as essentially the only reaction medium throughout the reaction.

The organic solvent of the reaction medium may be any inert organic solvent in which the dialkyl acetone dicarboxylate and the pyrrole diester are highly soluble. However, it is preferably a halogenated or unhalogenated aliphatic or aromatic hydrocarbon having a boiling point in the range of about 30°–200° C., since such compounds, in addition to preventing solids formation, provide a convenient means of removing heat by operation at reflux. Illustrative of utilizable solvents are carbon tetrachloride, chloroform, methylene chloride, tetrachloroethane, ethylene dichloride, chlorobenzene, o-dichlorobenzene, the corresponding bromine compounds, benzene, xylene, toluene, etc. Methylene chloride is particularly preferred.

The acid employed in the practice of the invention may be any acid having a dissociation constant of at least $1.3 \times 10^{-5}$ at 25° C. Thus, it may be an inorganic acid, such as hydrochloric acid, sulfuric acid, etc., or a monofunctional or polyfunctional organic acid, such as formic, acetic, propionic, butanoic, pentanoic, hexanoic, glycolic, oxalic, malonic, succinic, glutaric, adipic, citric, etc. Either anhydrous or hydrous (typically 85–99%) acid may be used. The preferred acids are alkanoic acids containing 1–6 carbons, with formic acid being the alkanoic acid most preferred.

As mentioned above, the acid is used in a yield-enhancing amount. The particular amount optimally employed varies with various factors, such as the amounts of dialkyl acetone dicarboxylate, alkylamine, and water in the reaction mixture; but it is generally such as to provide an acid/dialkyl acetone dicarboxylate mol ratio in the range of about 0.25–3/1, preferably about 1–1.5/1, and a free amine/dialkyl acetone dicarboxylate mol ratio of at least about 3/1.

Except for the use of a yield-enhancing amount of acid, the process of the invention is conducted by known techniques, such as the techniques disclosed in the aforementioned patents and patent applications, the teachings of which are incorporated herein by reference. Thus, the ingredients of the reaction mixture are generally combined in amounts such as to provide a stoichiometric excess of the chloromethyl alkyl ketone and the alkylamine, usually such as to provide an alkylamine/dialkyl acetone dicarboxylate mol ratio of about 3–10/1, a chloromethyl akyl ketone/dialyl acetone dicarboxylate mol ratio of about 1–2/1, and an organic solvent/dialkyl acetone dicarboxylate mol ratio of about 5–30/1, and preferably such as to provide an alkylamine/dialkyl acetone dicarboxylate mol ratio of about 6/1 and an organic solvent/dialkyl acetone dicarboxylate mol ratio of about 8–15/1. The alkylamine may be aqueous or anhydrous, although anhydrous alkylamine is preferred when an essentially non-aqueous medium is employed because of its permitting better feed control.

The manner of combining the ingredients is not critical. Thus, the combination can be effected, e.g., by (A-1) charging solvent and acid to a suitable reaction vessel, conveniently one provided with a refrigerated condenser, (A-2) condensing or pressuring anhydrous alkylamine into the vessel at about 0°–30° C., or adding an aqueous solution of alkylamine, and (A-3) adding a mixture of dialkyl acetone dicarboxylate, chloromethyl alkyl ketone, and solvent; (B) sequentially adding the dialkyl acetone dicarboxylate, alkylamine, and chloromethyl alkyl ketone—each in portions of the solvent—to a reaction vessel containing the acid and the remainder of the solvent; (C) substantially simultaneously adding the dialkyl acetone dicarboxylate and chloromethyl alkyl ketone to a reaction vessel containing the acid and at least a portion of the alkylamine, preferably, at rates such as to provide a chloromethyl alkyl ketone/dialkyl acetone dicarboxylate mol ratio in the range of about 1.3–1.6/1 in the reaction mixture during the addition, etc.

Regardless of the particular method used to combine the ingredients, the reaction is generally conducted with agitation at reaction temperatures in the range of about 15°–65° C., preferably about 20°–40° C., until the reaction is completed. The agitation is sufficient to form a uniform dispersion of any solids formed during the reaction, and the temperature control prevents the formation of a solid intermediate that is typically formed at temperatures below about 15° C., while avoiding the yield decrease that would be expected to result from employing temperatures substantially in excess of about 65° C. However, temperatures in excess of 65° C. can be used if, for example, shorter reaction times are desired. Reaction times of about 0.5–2 hours are typical at the preferred reaction temperatures.

After the reaction has been completed, the pyrrole diester product can be recovered, purified, and/or further treated as desired. For example, the reaction mixture may be acidified or heated to distillation temperatures to eliminate excess amine, byproducts, and/or solvent; and water may be added to the reaction mixture after acidification or during distillation to dissolve any solid by-product that may have been formed. Alternatively, this by-product may be removed by filtration. After distillation, the pyrrole diester may be extracted from the reaction mixture by the use of a suitable extractant, such as the preferred organic solvents mentioned above.

When an essentially pure pyrrole diester is desired, the organic solvent can be stripped from the pyrrole diester after treatment with activated carbon and the pyrrole diester recrystallized.

The following procedures and examples are given to illustrate the invention and are not intended as a limitation thereof. In these procedures and examples, alphabetic designations are used for comparative examples and numeric designations for examples illustrating the invention, and certain abbreviations are used as defined below:

| Abbreviation | Definition |
| --- | --- |
| MADC | dimethyl acetone dicarboxylate |
| EADC | diethyl acetone dicarboxylate |
| n-PADC | di-n-propyl acetone dicarboxylate |
| i-PADC | di-isopropyl acetone dicarboxylate |
| BADC | di-n-butyl acetone dicarboxylate |
| CA | chloroacetone |
| MA | methylamine |
| MC | methylene chloride |
| PDE | pyrrole diester |
| VPC | vapor phase chromatography |

HETEROGENEOUS/SIMULTANEOUS ADDITION PROCEDURE

A suitable agitated reaction vessel provided with a branched feed line and maintained under a nitrogen atmosphere in a 20° C. water bath was simultaneously charged with (A) a 40% aqueous MA solution containing any acid to be used and (B) a solution of a dialkyl acetone dicarboxylate and CA in MC, the former being charged over a period of 25 minutes and the latter over a period of 30 minutes. The water bath was removed, and the mixture was agitated for another 30 minutes. Within a few minutes the small amount of solids formed during the reaction disappeared, and the temperature—which had already risen slightly during the reactant addition—rose still further to about 27°–30° C. Distilled water was then added, and a 95°–100° C. oil bath was placed around the vessel. MA and MC were distilled at 35°–93° C. over a period of about 30 minutes, after which the residue was cooled to 60°–65° C. and extracted with two portions of toluene. The extracts were combined and analyzed by VPC to determine the yield of PDE.

HETEROGENEOUS/SEQUENTIAL ADDITION PROCEDURE

This procedure was essentially the same as the simultaneous addition procedure described above except for the method of combining the reactants. In the sequential addition procedure, the reactants were combined by charging the reaction vessel with a 40% aqueous MA solution containing any acid to be used and then introducing a solution of the dialkyl acetone dicarboxylate and CA in MC below the surface of the MA solution.

HOMOGENEOUS PROCEDURE

A suitable agitated reaction vessel maintained under a nitrogen atmosphere was charged with MC and any acid to be used and cooled to 5° C. in an ice water bath. Then anhydrous MA was condensed into the solvent, and a solution of a dialkyl acetone dicarboxylate and CA in MC was fed under the surface of the MA solution over a period of one hour while allowing the temperature to rise, generally to about 25°–30° C. Solids were formed at temperatures below 15° C. but disappeared at temperatures above 20° C. The water bath was then removed, and agitation was continued for another hour at the desired reaction temperature. Subsequently a 95°–100° C. oil bath was placed around the vessel, and MA and MC were distilled at about 40°–60° C. over a period of one hour. Hot distilled water was added to the vessel, which contained a slurry of MA hydrochloride in liquid, and distillation was continued for an additional 20 minutes to a final temperature of about 92° C. The residue was cooled to about 80° C. and then extracted with two portions of cold toluene. The extracts were then combined and analyzed by VPC to determine the yield of PDE.

COMPARATIVE EXAMPLE A

Thirteen samples of ethyl 1,4-dimethyl-3-ethoxycarbonylpyrrole-2-acetate were prepared by the heterogeneous/simultaneous addition procedure described above, using no acid, one molar proportion of EADC as the dialkyl acetone dicarboxylate, 10.7 molar proportions of MC as the solvent, and amounts of CA and MA such as to provide the CA/EADC and MA/EADC mole ratios shown in Table I. The yields of PDE obtained in each run are shown in Table I.

TABLE I

| Run No. | CA/EADC | MA/EADC | PDE Yield, % |
|---|---|---|---|
| A-1 | 1.5 | 4.0 | 71 |
| A-2 | 1.3 | 4.5 | 67.5 |
| A-3 | 1.4 | 4.5 | 70 |
| A-4 | 1.5 | 4.5 | 68.2 |
| A-5 | 1.5 | 4.5 | 71 |
| A-6 | 1.5 | 4.5 | 68.5 |
| A-7 | 1.5 | 4.5 | 69 |
| A-8 | 1.5 | 6.0 | 65.5 |
| A-9 | 1.5 | 6.0 | 32.5 |
| A-10 | 1.5 | 6.0 | 68 |
| A-11 | 1.5 | 6.0 | 64.5 |
| A-12 | 1.5 | 8.0 | 62.5 |
| A-13 | 1.5 | 9.0 | 64 |

EXAMPLE I

Another fourteen samples of ethyl 1,4-dimethyl-3-ethoxycarbonylpyrrole-2-acetate were prepared by the heterogeneous/simultaneous addition procedure described above, using one molar proportion of EADC as the dialkyl acetone dicarboxylate, 10.7 molar proportions of MC as the solvent, and amounts of acid, CA, and MA such as to provide the acid/EADC, CA/EADC, and MA/EADC mol ratios shown in Table II. The particular acids employed and the yields of PDE obtained are also shown in that table.

TABLE II

| Run No. | Acid | Acid/EADC | CA/EADC | MA/EADC | PDE Yield % |
|---|---|---|---|---|---|
| A-14 | HCl | 4.5 | 1.5 | ~4.5 | 5.5 |
| 1 | HCl | 1.5 | 1.5 | 6.0 | 73 |
| 2 | Sulfuric | 0.75 | 1.5 | 6.0 | 73 |
| 3 | Formic | 0.5 | 1.5 | 5.0 | 72.5 |
| 4 | Formic | 1.5 | 1.5 | 6.0 | 77.5 |
| 5 | Formic | 1.5 | 1.5 | 6.0 | 74 |
| 6 | Formic | 1.5 | 1.5 | 6.0 | 72.5 |
| 7 | Formic | 1.5 | 1.5 | 6.0 | 70 |
| 8 | Formic | 1.5 | 1.5 | 7.5 | 69 |
| 9 | Acetic | 0.25 | 1.5 | 4.5 | 72.5 |
| 10 | Acetic | 1.5 | 1.5 | 6.0 | 72 |
| 11 | Acetic | 2.0 | 1.4 | 8.0 | 71.5 |
| 12 | Oxalic | 0.75 | 1.5 | 6.0 | 72 |
| 13 | Glycolic | 1.5 | 1.5 | 6.0 | 73 |

EXAMPLE II

Twelve samples of pyrrole diesters were prepared by the heterogeneous/simultaneous addition procedure described above, using one molar proportion of the dialkyl acetone dicarboxylate (ADC), 10.7 molar proportions of MC as the solvent, and amounts of formic acid, CA, and MA such as to provide the acid/ADC, CA/ADC, and MA/ADC mol ratios shown in Table III. The particular dialkyl acetone dicarboxylates employed and the yields of PDE obtained are also shown in that table.

TABLE III

| Run No. | ADC | Acid/ADC | CA/ADC | MA/ADC | PDE Yield, % |
|---|---|---|---|---|---|
| A-15 | MADC | 0 | 1.5 | 6.0 | 33.5 |
| 14 | MADC | 1.5 | 1.4 | 5.0 | 52 |
| 15 | MADC | 1.5 | 1.4 | 5.5 | 52 |
| 16 | MADC | 4 | 1.4 | 8.0 | 49 |
| A-16 | n-PADC | 0 | 1.5 | 6.0 | 75 |
| 17 | n-PADC | 1.5 | 1.4 | 5.5 | 81 |
| 18 | n-PADC | 1.5 | 1.4 | 6.0 | 80.5 |
| A-17 | i-PADC | 0 | 1.5 | 6.0 | 74 |

TABLE III-continued

| Run No. | ADC | Acid/ADC | CA/ADC | MA/ADC | PDE Yield, % |
|---|---|---|---|---|---|
| 19 | i-PADC | 1.5 | 1.4 | 5.5 | 76.5 |
| 20 | i-PADC | 1.5 | 1.4 | 6.0 | 79 |
| A-18 | BADC | 0 | 1.5 | 6.0 | 71.5 |
| 21 | BADC | 1.5 | 1.4 | 6.0 | 77.5 |

EXAMPLE III

Five samples of ethyl 1,4-dimethyl-3-ethoxycarbonylpyrrole-2-acetate were prepared by the heterogeneous/sequential addition procedure described above, using one molar proportion of EADC as the dialkyl acetone dicarboxylate, 10.7 molar proportions of MC as the solvent, and amounts of acid, CA, and MA such as to provide the acid/EADC, CA/EADC, and MA/EADC mol ratios shown in Table IV. The particular acids employed and the yields of PDE obtained are also shown in that table.

TABLE IV

| Run No. | Acid | Acid/EADC | CA/EADC | MA/EADC | PDE Yield, % |
|---|---|---|---|---|---|
| A-19 | None | 0 | 1.4 | 8.0 | 61.5 |
| 22 | Formic | 1.5 | 1.4 | 6.0 | 74.5 |
| 23 | Formic | 1.5 | 1.5 | 6.0 | 74.5 |
| 24 | Citric | 0.5 | 1.5 | 6.0 | 72.5 |

COMPARATIVE EXAMPLE B

Thirteen samples of ethyl 1,4-dimethyl-3-ethoxycarbonylpyrrole-2-acetate were prepared by the homogeneous procedure described above, using no acid, one molar proportion of EADC as the dialkyl acetone dicarboxylate, 1.4 molar proportions of CA, and amounts of MA and MC such as to provide the MA/EADC and MC/EADC mol ratios shown in Table V. The reaction temperatures employed and the yields of PDE obtained are also shown in that table.

TABLE V

| Run No. | MA/EADC | MC/EADC | Temp., °C. | PDE Yield, % |
|---|---|---|---|---|
| B-1 | <5 | 15 | 15 | 15.5 |
| B-2 | 5 | 13.4 | 20 | 67 |
| B-3 | >5 | 10.7 | 15 | 57 |
| B-4 | >5 | 15 | 15 | 62 |
| B-5 | >5 | 15 | 15 | 64.5 |
| B-6 | 6 | 15 | 25 | 68 |
| B-7 | 6 | 15 | 30 | 64 |
| B-8 | 6 | 15 | 30 | 66.5 |
| B-9 | 6 | 15 | 30 | 67 |
| B-10 | 6 | 15 | 35 | 65.5 |
| B-11 | 6 | 15 | 38 | 68.5 |
| B-12 | 6 | 13.5 | 30 | 62 |
| B-13 | 6 | 14 | 25 | 72 |

EXAMPLE IV

A sample of ethyl 1,4-dimethyl-3-ethoxycarbonylpyrrole-2-acetate was prepared by the homogeneous procedure generally described above, using 1.5 molar proportions of formic acid, one molar proportion of EADC, 1.4 molar proportions of CA, 5 molar proportions of MA, 15 molar proportions of MC, and a reaction temperature of 20° C. The PDE yield was 77%.

This invention is susceptible to considerable variation within the spirit and scope of the appended claims.

I claim:

1. In a process for preparing an alkyl 1,4-dialkyl-3-alkoxycarbonylpyrrole-2-acetate corresponding to the formula:

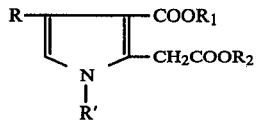

by reacting a chloromethyl alkyl ketone of the formula ClCH₂COR with a dialkyl acetone dicarboxylate corresponding to the formula:

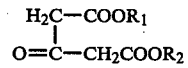

and an alkylamine of the formula R'NH₂, in which the formulas R, R', R₁, and R₂ are independently selected from lower alkyl groups, said reaction being conducted in a reaction medium comprising an organic solvent; the improvement which comprises conducting the reaction in the presence of a yield-enhancing amount of an acid having a dissociation constant of at least $1.3 \times 10^{-5}$ at 25° C.

2. The process of claim 1 wherein the chloromethyl alkyl ketone is chloroacetone.

3. The process of claim 1 wherein the dialkyl acetone dicarboxylate is diethyl acetone dicarboxylate.

4. The process of claim 1 wherein the alkylamine is methylamine.

5. The process of claim 4 wherein the methylamine is anhydrous methylamine.

6. The process of claim 1 wherein the organic solvent is methylene chloride.

7. The process of claim 1 wherein the acid is an alkanoic acid containing 1–6 carbons.

8. The process of claim 7 wherein the alkanoic acid is formic acid.

9. The process of claim 1 wherein the ingredients of the reaction mixture are contacted in amounts such as to provide an acid/dialkyl acetone dicarboxylate mol ratio of about 0.25–3/1 and a free amine/dialkyl acetone dicarboxylate mol ratio of at least about 3/1.

10. The process of claim 1 wherein the chloromethyl alkyl ketone is chloroacetone, the dialkyl acetone dicarboxylate is diethyl acetone dicarboxylate, the alkylamine is methylamine, and the acid is formic acid.

11. In a process for preparing an alkyl 1,4-dialkyl-3-alkoxycarbonylpyrrole-2-acetate corresponding to the formula:

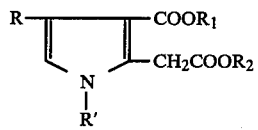

by reacting a chloromethyl alkyl ketone of the formula ClCH₂COR with a dialkyl acetone dicarboxylate corresponding to the formula:

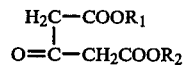

and an alkylamine of the formula R'NH$_2$, in which formulas R, R', R$_1$ and R$_2$ are independently selected from lower alkyl groups, said reaction being conducted in a reaction medium consisting essentially of an organic solvent; the improvement which comprises conducting the reaction in the presence of a yield-enhancing amount of an acid having a dissociation constant of at least $1.3 \times 10^{-5}$ at 25° C.

12. The process of claim 11 wherein the ingredients of the reaction mixture are contacted in amounts such as to provide an acid/dialkyl acetone dicarboxylate mol ratio of about 0.25–3/1 and a free amine/dialkyl acetone dicarboxylate mol ratio of at least about 3/1.

13. The process of claim 11 wherein the chloromethyl alkyl ketone is chloroacetone, the dialkyl acetone dicarboxylate is diethyl acetone dicarboxylate, the alkylamine is anhydrous methylamine, the acid is formic acid, and the organic solvent is methylene chloride.

14. In a process for preparing an alkyl 1,4-dialkyl-3-alkoxycarbonylpyrrole-2-acetate corresponding to the formula:

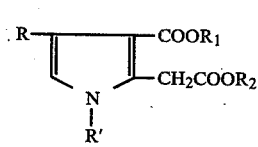

by reacting a chloromethyl alkyl ketone of the formula ClCH$_2$COR with a dialkyl acetone dicarboxylate corresponding to the formula:

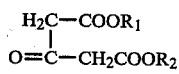

and an alkylamine of the formula R'NH$_2$, in which formulas R, R', R$_1$, and R$_2$ are independently selected from lower alkyl groups, said reaction being conducted in a reaction medium comprising an organic solvent and water; the improvement which comprises conducting the reaction in the presence of a yield-enhancing amount of an acid having a dissociation constant of at least $1.3 \times 10^{-5}$ at 25° C.

15. The process of claim 14 wherein the ingredients of the reaction mixture are contacted in amounts such as to provide an acid/dialkyl acetone dicarboxylate mol ratio of about 0.25–3/1 and a free amine/dialkyl acetone dicarboxylate mol ratio of at least about 3/1.

16. The process of claim 14 wherein the chloromethyl alkyl ketone is chloroacetone, the dialkyl acetone dicarboxylate is diethyl acetone dicarboxylate, the alkylamine is methylamine, the acid is formic acid, and the organic solvent is methylene chloride.

* * * * *